US00PP32201P2

(12) United States Plant Patent
Koot

(10) Patent No.: US PP32,201 P2
(45) Date of Patent: Sep. 15, 2020

(54) ***CALIBRACHOA* PLANT NAMED 'DOCALHUSOPIN 19'**

(50) Latin Name: ***Calibrachoa* X *hybrida***
Varietal Denomination: Docalhusopin 19

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,353

(22) Filed: Sep. 23, 2019

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02
See application file for complete search history.

(56) References Cited

PUBLICATIONS

PLUTO Plant Variety Databse Mar. 26, 2010. p. 1.*

* cited by examiner

*Primary Examiner* — Annette H Para
(74) *Attorney, Agent, or Firm* — C. A. Whealy

(57) ABSTRACT

A new and distinct cultivar of *Calibrachoa* plant named 'Docalhusopin 19', characterized by its semi-upright to outwardly spreading, trailing and decumbent plant habit; vigorous growth habit; freely branching habit; early and freely flowering habit; large flowers with light red purple-colored petals with dark red purple-colored centers; and good garden performance.

2 Drawing Sheets

Figure 1:
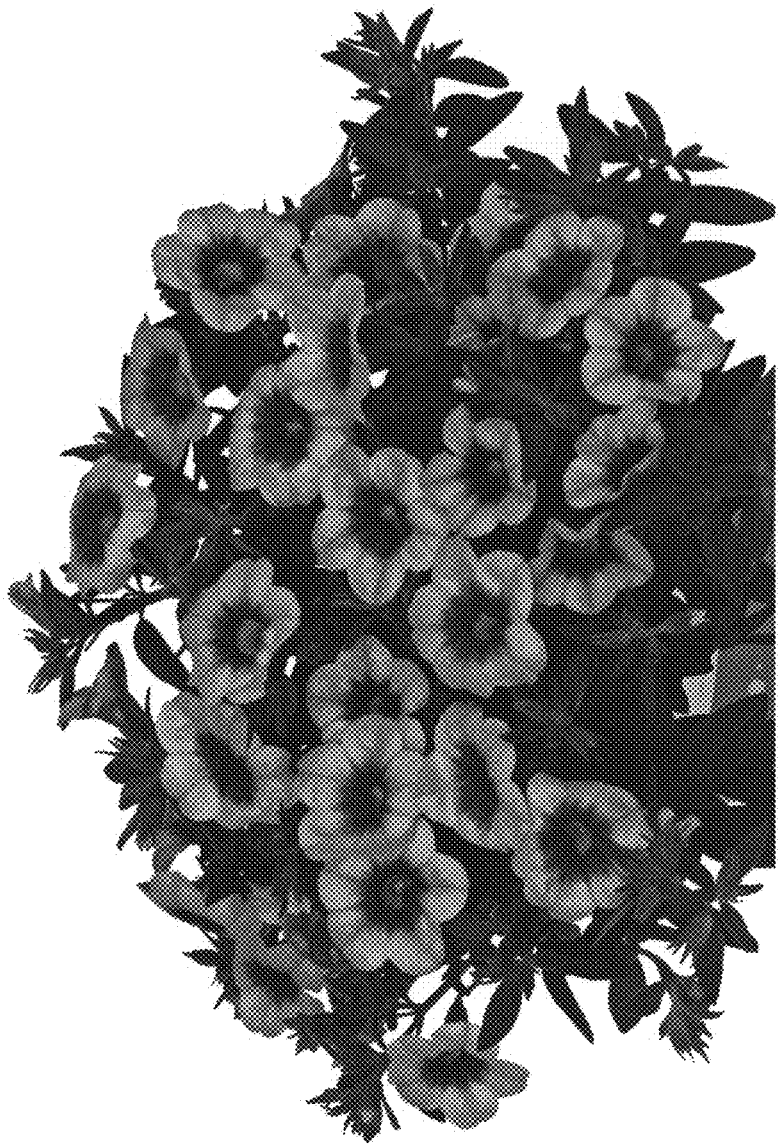

Botanical designation: *Calibrachoa* X *hybrida.*
Cultivar denomination: 'DOCALHUSOPIN 19'.

BACKGROUND OF THE INVENTION

The present invention relates to a new and distinct cultivar of *Calibrachoa* plant, botanically known as *Calibrachoa* X *hybrida* and hereinafter referred to by the name 'Docalhusopin 19'.

The new *Calibrachoa* plant is a product of a planned breeding program conducted by the Inventor in Rheinberg, Germany. The objective of the breeding program is to create new freely branching and early-flowering *Calibrachoa* plants with numerous attractive flowers.

The new *Calibrachoa* plant originated from a cross-pollination made by the Inventor in July, 2016 in Rheinberg, Germany of a proprietary selection of *Calibrachoa* X *hybrida* identified as code number AA15-005956-002, not patented, as the female, or seed, parent with a proprietary selection of *Calibrachoa* X *hybrida* identified as code number AA14-007028-003, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2018.

Asexual reproduction of the new *Calibrachoa* plant by vegetative terminal cuttings in a controlled greenhouse environment in Rheinberg, Germany since June, 2018 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Docalhusopin 19'. These characteristics in combination distinguish 'Docalhusopin 19' as a new and distinct *Calibrachoa* plant:

1. Semi-upright to outwardly spreading, trailing and decumbent plant habit.
2. Vigorous growth habit.
3. Freely branching habit.
4. Early and freely flowering habit.
5. Large flowers with light red purple-colored petals with dark red purple-colored centers.
6. Good garden performance.

The new *Calibrachoa* can be compared to plants of the female parent selection. Plants of the new *Calibrachoa* differ primarily from plants of the female parent selection in the following characteristics:

1. Plants of the new *Calibrachoa* have larger flowers than plants of the female parent selection.
2. Flowers of plants of the new *Calibrachoa* are lighter red purple in color than flowers of plants of the female parent selection.

The new *Calibrachoa* can be compared to plants of the male parent selection. Plants of the new *Calibrachoa* differ primarily from plants of the male parent selection in the following characteristics:

1. Plants of the new *Calibrachoa* have larger flowers than plants of the male parent selection.

2. Flowers of plants of the new *Calibrachoa* are light red purple and dark red purple in color whereas flowers of plants of the male parent selection have red-colored flowers.

Plants of the new *Calibrachoa* can be compared to plants of *Calibrachoa* sp. 'Mini Famous Red+Pink Eye', not patented. In side-by-side comparisons, plants of the new *Calibrachoa* differ primarily from plants of 'Mini Famous Red+Pink Eye' in the following characteristics:

1. Plants of the new *Calibrachoa* have thicker lateral branches than plants of 'Mini Famous Red+Pink Eye'.
2. Plants of the new *Calibrachoa* have longer and darker green-colored leaves than plants of 'Mini Famous Red+Pink Eye'.
3. Plants of the new *Calibrachoa* are more freely flowering than plants of 'Mini Famous Red+Pink Eye'.
4. Plants of the new *Calibrachoa* have larger flowers than plants of 'Mini Famous Red+Pink Eye'.
5. Plants of the new *Calibrachoa* and 'Mini Famous Red+Pink Eye' differ in flower color as plants of 'Mini Famous Red+Pink Eye' have lighter-colored flowers.
6. Plants of the new *Calibrachoa* have larger sepals than plants of 'Mini Famous Red+Pink Eye'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1 of 2) is a side perspective view of a typical flowering plant of 'Docalhusopin 19' grown in a container.

Figure 2:
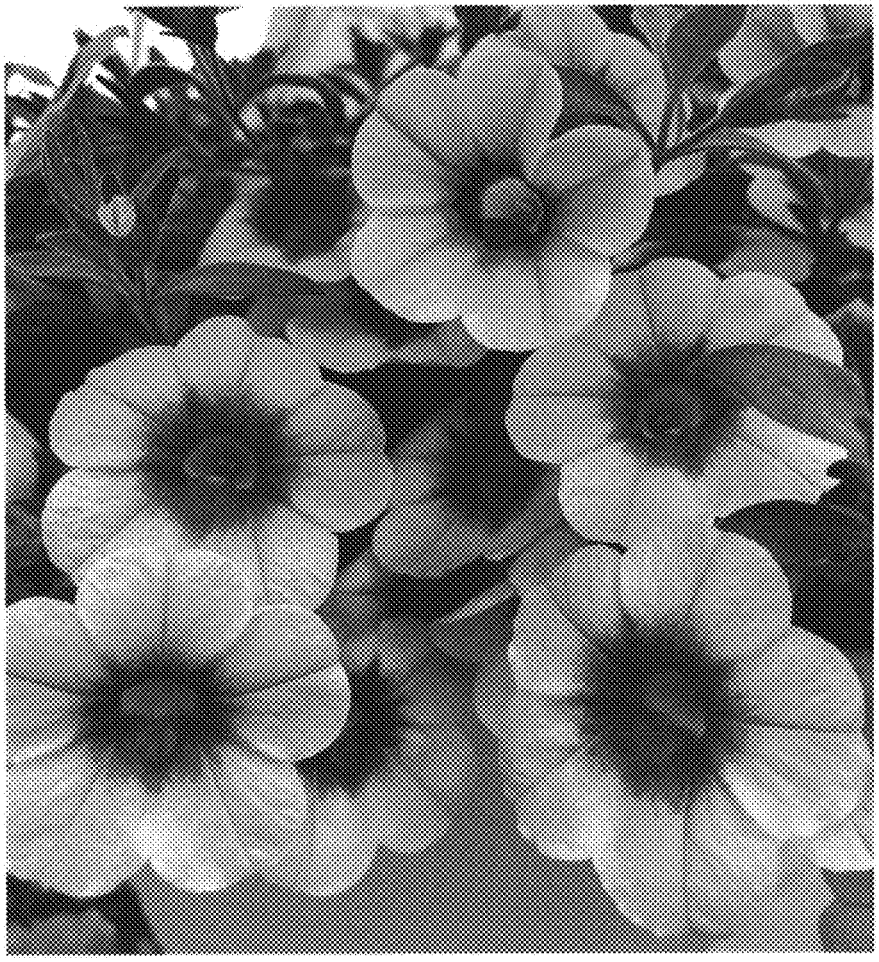

The photograph on the second sheet (FIG. 2 of 2) is a close-up view of typical flowers of 'Docalhusopin 19'.

DETAILED BOTANICAL DESCRIPTION

The aforementioned photographs and following observations, measurements and values describe plants grown during the spring in 13-cm containers in a glass-covered greenhouse in Rheinberg, Germany and under cultural practices typical of commercial *Calibrachoa* production. During the production of the plants, day and night temperatures averaged 18° C. and light levels averaged 1,500 lux. Rooted young plants were pinched one time three weeks after planting and were twelve weeks old when the photographs and description were taken. In the following description, color references are made to The Royal Horticultural Society Colour Chart, Fifth Edition, except where general terms of ordinary dictionary significance are used.

Botanical classification: *Calibrachoa* X *hybrida* 'Docalhusopin 19'.

Parentage:

*Female, or seed, parent*.—Proprietary selection of *Calibrachoa* X *hybrida* identified as code number AA15-005956-002, not patented.

*Male, or pollen, parent*.—Proprietary selection of *Calibrachoa* X *hybrida* identified as code number AA14-007028-003, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Semi-upright to outwardly spreading to trailing and decumbent plant habit; freely branching habit with about 9 to 10 primary lateral branches each with about 11 to 14 secondary lateral branches developing per plant; pinching enhances branching; dense and full appearance; vigorous growth habit; moderate growth rate.

*Plant height, soil level to top of foliar plane*.—About 14 cm.

*Plant height, soil level to top of floral plane*.—About 14 cm.

*Plant diameter* (*spread of plant*).—About 38 cm.

Lateral branch description:

*Length*.—About 11 cm.

*Diameter*.—About 3.5 mm.

*Internode length*.—About 1.8 cm.

*Strength*.—Strong.

*Aspect*.—Initially upright to outwardly spreading to trailing and decumbent.

*Texture and luster*.—Pubescent; glossy.

*Color, developing*.—Close to 145B.

*Color, developed*.—Close to 145A; at the internodes, close to 142A.

Leaf description:

*Arrangement*.—Before flowering, alternate, and after flowering, opposite; simple.

*Length*.—About 3.2 cm.

*Width*.—About 1.3 cm.

*Shape*.—Oblanceolate.

*Apex*.—Rounded.

*Base*.—Attenuate.

*Margin*.—Entire.

*Texture and luster, upper and lower surfaces*.—Pubescent; matte.

*Venation pattern*.—Pinnate; arcuate.

*Color*.—Developing leaves, upper surface: Close to 143B. Developing leaves, lower surface: Close to 143C. Fully expanded leaves, upper surface: Close to 137A; venation, close to 144B. Fully expanded leaves, lower surface: Close to 138B; venation, close to 142B.

*Petioles*.—Length: About 1.6 mm. Diameter: About 1.3 mm. Strength: Moderately strong. Texture and luster, upper and lower surfaces: Pubescent; matte. Color, upper surface: Close to 145A. Color, lower surface: Close to 145B.

Flower description:

*Flower arrangement and habit*.—Single salverform flowers arising from leaf axils; freely flowering habit with usually about 40 flowers and about 18 flower buds per plant during the flowering season; flowers face upright to outwardly.

*Fragrance*.—None detected.

*Natural flowering season*.—Early flowering habit, plants of the new *Calibrachoa* initiate and develop flowers about six weeks after planting; plants flower continuously from the spring throughout the summer in Germany.

*Flower longevity*.—Individual flowers last about seven to ten days on the plant; flowers not persistent.

*Flower buds*.—Length: About 2.4 cm. Diameter: About 4.8 mm. Shape: Elongated oblong. Texture and luster: Rippled, pubescent; semi-glossy. Color: Close to 154C and 70A.

*Flower diameter*.—About 3.7 cm.

*Flower depth* (*height*).—About 2 cm.

*Flower throat diameter*.—About 1.1 cm.

*Flower tube length*.—About 1.7 cm.

*Flower tube diameter*.—About 1 mm.

*Corolla*.—Arrangement: Five petals fused at the base and opening into a flared trumpet. Petal length from throat: About 1.9 cm. Petal lobe width: About 1.6 cm. Petal shape: Roughly spatulate. Petal apex: Rounded. Petal margin: Entire; slightly undulate. Petal texture and luster, upper and lower surfaces: Smooth, glabrous; matte. Throat texture: Smooth, glabrous. Tube texture: Smooth, glabrous. Color: Petal, when opening, upper surface: Distally, close to 64D; towards the throat, close to 79A and N57A. Petal, when opening, lower surface: Close to N57D. Petal, fully opened, upper surface: Distally, close to 64D; towards the throat, close to N57A; venation, close to N57A; center color becoming closer to N81A with development. Petal, fully opened, lower surface: Close to 74C; venation, close to 145C; color becoming closer to N80C with development. Throat: Close to 9B; venation, close to 150D. Tube: Close to 1C; venation, close to 150D.

*Calyx*.—Arrangement: Star-shaped calyx with five sepals; sepals fused at the base. Sepal length: About 1.5 cm. Sepal width: About 3 mm. Sepal shape: Lanceolate. Sepal apex: Acute. Sepal margin: Entire. Sepal texture and luster, upper and lower surfaces: Pubescent; matte. Color: When developing and fully developed, upper surface: Close to 143A. When developing and fully developed, lower surface: Close to 143B.

*Peduncles*.—Length: About 2 cm. Diameter: About 1.5 mm. Angle: About 45° from stem axis. Strength: Moderately strong. Texture and luster: Pubescent; matte. Color: Close to 145A.

*Reproductive organs*.—Stamens: Quantity: Five per flower. Filament length: About 8 mm. Filament color: Close to 149D. Anther length: About 1 mm. Anther shape: Ellipsoidal. Anther color: Close to 14B. Pollen amount: Scarce. Pollen color: Close to 9A. Pistils: Quantity: One per flower. Pistil length: About 1.1 cm. Style length: About 9 mm. Style color: Close to 145C. Stigma diameter: About 1 mm. Stigma shape: Ellipsoidal. Stigma color: Close to 143B. Ovary color: Close to 141D. Fruits: Quantity produced per plant: About ten during the flowering season. Length: About 6 mm. Diameter: About 4 mm. Texture: Smooth, glabrous. Color: Close to N199C. Seeds: Quantity per flower: About 55. Length: About 1 mm. Diameter: About 1 mm. Texture: Smooth, glabrous. Color: Close to 200A.

Garden performance: Plants of the new *Calibrachoa* have been observed to have good garden performance and to tolerate wind, rain, temperatures ranging from about 3° C. to about 28° C. and to be suitable for USDA Hardiness Zone 11.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Docalhusopin 19' as illustrated and described.

* * * * *